(12) United States Patent
Chenger et al.

(10) Patent No.: US 9,427,288 B1
(45) Date of Patent: Aug. 30, 2016

(54) CONTAINMENT SHIELD FOR SURGICAL INSTRUMENTS

(71) Applicants: Joseph Chenger, Nashville, TN (US); Paul Yahnian, Nashville, TN (US)

(72) Inventors: Joseph Chenger, Nashville, TN (US); Paul Yahnian, Nashville, TN (US)

( * ) Notice: Subject to any disclaimer, the term of this patent is extended or adjusted under 35 U.S.C. 154(b) by 615 days.

(21) Appl. No.: 13/742,587

(22) Filed: Jan. 16, 2013

(51) Int. Cl.
*A61B 17/32* (2006.01)
*A61B 19/08* (2006.01)

(52) U.S. Cl.
CPC .................................. *A61B 19/081* (2013.01)

(58) Field of Classification Search
CPC .... A61B 19/081; A61B 19/10; A61B 19/42; A61F 2013/00297; A61F 2013/00306; A61M 2025/0273; A61M 25/02; C11C 5/006
See application file for complete search history.

(56) References Cited

U.S. PATENT DOCUMENTS

| | | | |
|---|---|---|---|
| 4,898,588 A | 2/1990 | Roberts | |
| 4,926,882 A | 5/1990 | Lawrence | |
| 4,949,734 A | 8/1990 | Bernstein | |
| 5,250,064 A | 10/1993 | Schneider | |
| 5,275,559 A | 1/1994 | Rihel | |
| 5,288,231 A * | 2/1994 | Kuehn et al. | 433/29 |
| 5,388,593 A | 2/1995 | Thomalla | |
| 5,522,403 A | 6/1996 | Bark et al. | |
| 5,542,435 A | 8/1996 | Kelly et al. | |
| D399,971 S | 10/1998 | Scherer | |
| 6,210,261 B1 | 4/2001 | Johnson | |
| 2004/0097996 A1* | 5/2004 | Rabiner et al. | 606/159 |
| 2006/0292522 A1 | 12/2006 | Lees et al. | |
| 2009/0241855 A1* | 10/2009 | Stocki et al. | 119/815 |
| 2010/0024745 A1* | 2/2010 | Harlow | 119/856 |
| 2011/0277701 A1* | 11/2011 | King | 119/815 |
| 2011/0313370 A1 | 12/2011 | Smyth | |

* cited by examiner

*Primary Examiner* — Ashley Fishback
(74) *Attorney, Agent, or Firm* — Ryan D. Levy; Patterson Intellectual Property Law, P.C.

(57) ABSTRACT

A disposable containment shield is operable to mount on an output housing of a surgical cutting instrument to keep spatter off of a surgeon's face shield enabling quick and complete restoration of visibility while cutting biological material. The containment shield includes a body that is substantially transparent and has a generally consistent thickness such that the body is pliable and resilient. The body is substantially planar and sterile when in the package. The containment shield forms into a three dimensional shape having a distal face and a proximal face, and a mounting hole of the containment shield engages onto the output housing of the surgical cutting instrument such that the distal face is at an acute angle with respect to a longitudinal axis through the mounting hole and faces toward a cutting device of the surgical cutting instrument.

10 Claims, 5 Drawing Sheets

CONTAINMENT SHIELD FOR SURGICAL INSTRUMENTS

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

This invention relates to an apparatus and method which provide for a disposable containment shield. More particularly, the invention relates to a disposable containment shield that may be packaged and shipped in a substantially flat, sterilized configuration and may be mounted to any surgical cutting instrument.

Orthopedic surgery often involves cutting hard biological tissues such as bone or cartilage. Orthopedic surgeons frequently use power tools to increase the speed and accuracy of surgical procedures which results in better patient outcomes. These power tools often include surgical cutting instruments such as saws, drills, chisels, pneumatic hammers, grinders, cutting wheels, and rotary cutting tools (e.g., a Dremel™ tool). These and other surgical cutting instruments cause spatter of biological material including blood, bone fragments, soft tissue, etc. To prevent the spread of disease, machines in the operating room are covered with surgical drapes, and orthopedic surgeons and other surgical personnel wear full surgical outfits including a gown, gloves, a hat, and a face shield. The surgeon, a nurse, or other operating room personnel must frequently clean the orthopedic surgeon's face shield to maintain visibility while the surgeon is using a surgical cutting instrument. Even with frequent cleaning, visibility is often reduced due to inadequate cleaning. This slows down orthopedic surgical procedures and may negatively impact surgical outcomes. Furthermore, the use of instruments for orthopedic surgery may result in spatter of biological material in a large area within an operating room. This can further complicate the surgical procedure as well as the subsequent cleaning of the operating room.

Additionally, the spattered material may rebound off of one or more items that it impacts, particularly if the spattered material is bone fragment. Thus, even with current protective gear in use, it is possible for operating room personnel to be injured by spattered material (e.g., bounce off of a face shield into an eye of someone in the operating room). Further, this rebounding effect can leave an operating room spattered not only on equipment and personnel facing the patient or subject, but also on the back, top, and underside of the equipment and personnel in the operating room making the operating room very messy and time consuming to clean. Additionally, secondary contamination can result from drippings off the ceiling or other areas and possibly infect a subsequent patient.

BRIEF SUMMARY OF THE INVENTION

In one aspect of the invention, the zone of biological material spatter and the amount of debris, both biologic and non-biologic including smoke and vapors, may be reduced during the procedures (which may involve surgical cutting instruments) by affixing a disposable containment shield to the surgical cutting instrument. The disposable containment shield substantially blocks or contains spatter from impacting the patient or subject, operating room personnel, and operating room equipment (i.e., primary contamination). The containment shield also decreases or eliminates secondary contamination in the operation room.

In another aspect, a containment shield is operable to mount on an output housing of the surgical cutting instrument. The containment shield includes a body. The body has a distal face and a proximal face. The body is substantially transparent and has a generally consistent thickness such that the body is pliable and resilient. The body may have a plurality of folds, and adjacent folds may be in opposite directions with respect to the distal and proximal faces. The body has a mounting hole operable to engage the output housing of the surgical instrument. When mounted on the output housing of the surgical cutting instrument, the distal face is at an acute angle with respect to a longitudinal axis through the mounting hole and faces toward a cutting device of the surgical cutting instrument. The proximal face is at an obtuse angle with respect to the longitudinal axis and faces toward housing side of the surgical cutting instrument.

In another aspect, a containment shield is operable to mount on an output housing of various other surgical instruments. The containment shield includes a body having a distal face, a proximal face, a tab, and a slot. The body may be substantially transparent and may have a generally consistent thickness such that the body is pliable and resilient. The body is generally conical when the tab is inserted in the slot, and the body may be substantially flat when the tab is not in the slot. The body has a mounting hole formed when the tab is in the slot, and the mounting hole is operable to engage the output housing of the surgical cutting instrument. When the tabs are within the slots and the body is mounted on the output housing of the surgical cutting instrument, the distal face is at an acute angle with respect to a longitudinal axis through the mounting hole and faces toward a cutting device of the surgical cutting instrument. The proximal face is at an obtuse angle with respect to the longitudinal axis and faces toward a housing side of the surgical cutting instrument.

In another aspect, a method of using a containment shield is disclosed. The containment shield is operable to mount on an output housing of the surgical cutting instrument. The method begins with removing the containment shield from packaging. The shield includes a body that is substantially transparent and has a generally consistent thickness such that the body is pliable and resilient. The body is substantially planar and sterile when in the package. The containment shield is then formed into a three-dimensional shape having a distal face and a proximal face. A mounting hole of the containment shield is engaged on the output housing of the surgical cutting instrument such that the distal face is at an acute angle with respect to a longitudinal axis through the mounting hole and faces toward a cutting device of the surgical cutting instrument. The proximal face is at an obtuse angle with respect to the longitudinal axis and faces toward a housing side of the surgical cutting instrument.

In another aspect, the containment shield may include a port that may be used with a suction device. Such port may be used to assist in removing smoke, vapor, and airborne particulate from within the containment shield.

In another aspect, the containment shield may include a coating or be formed from a material that may reduce glare. Additionally, the containment shield may be used with a laser or other optic device which may improve visibility and provide for increased safety.

BRIEF DESCRIPTION OF THE SEVERAL VIEWS OF THE DRAWINGS

The accompanying drawings are incorporated in and constitute a part of this specification. The drawings illustrate optional embodiments of the invention and together with the description serve to explain some principles of the invention.

Reference will now be made in detail to optional embodiments of the invention, examples of which are illustrated in accompanying drawings. Whenever possible, the same reference numbers are used in the drawing and in the description referring to the same or like parts.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims. As used herein, "fold" is intended to refer to a fold, crease, or other joint. Furthermore, as used herein the term "containment shield" includes but is not limited to embodiments that contain elements during surgical procedures or the like. This can include fluids, debris, smoke, certain wavelengths of light, Biologic and non-biological material. The term "containment shield" can also be understood as a device that at least partially assists in blocking spatter, which may include the splashing or impact of biological and non-biological material against the shield.

Figure 1:
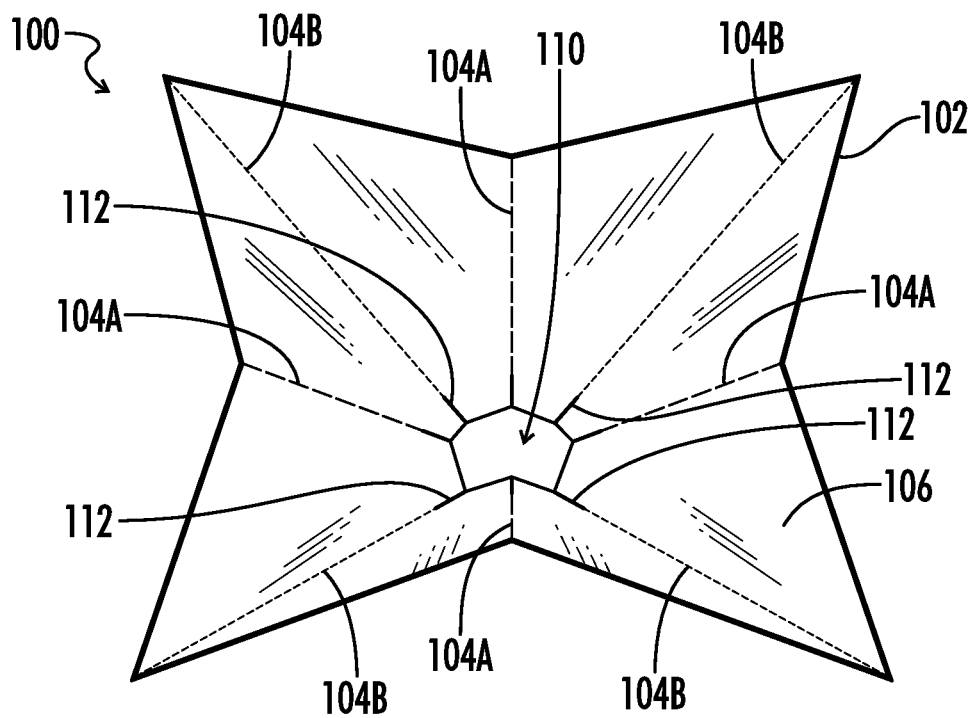
FIG. 1 is a perspective view of a distal face of a containment shield.
Figure 4:
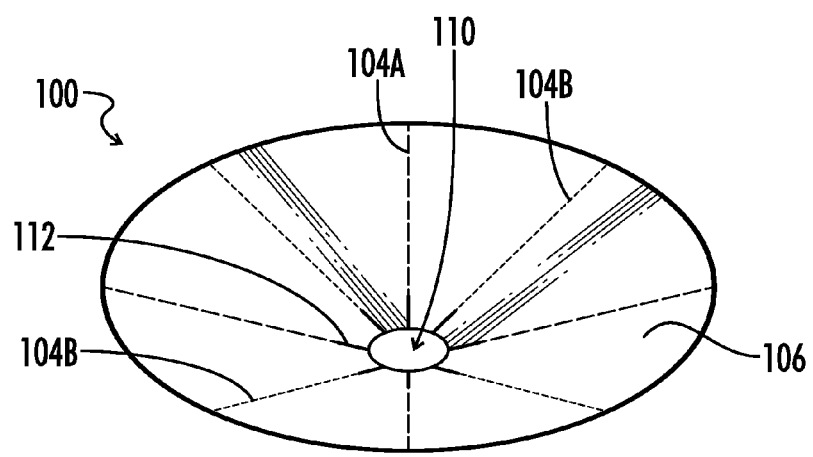
FIG. 4 is a perspective view of a distal face of a containment shield.

Referring to FIGS. 1 and 4, a containment shield 100 is operable to mount on an output housing of a surgical cutting instrument. As used herein, a surgical cutting instrument is any tool used in human or veterinary surgery, organ harvesting, or autopsy that may result in spatter or release of biological material such as a saw, drill, chisel, hammer, screwdriver, grinder, cutting wheel, laser cutting tools, laser coagulators, cauterizing devices, water pulsating device, rasp, pliers, organ harvesting tools, tissue harvesting tools, impactors, dental tools, or rotary cutting tool such as a Dremel™ tool. Such surgical cutting instruments may be used primarily on biological tissue (e.g., removing bone spurs, fragments, etc.) or on foreign objects (e.g., screws, plates, wires, fusion devices, etc.). The containment shield 100 includes a body 102 having a distal face 106 and a proximal face 108. The body 102 is substantially transparent and has a generally consistent thickness such that the body 102 is pliable and resilient. Optionally, the thickness may range from about 0.005 inches to about 0.05 inches thick with many optional embodiments being around 0.015 inches thick. Optionally, the thickness may depend on the specific application for which the device will be used. The thickness range is only an example and in some optional embodiments, the device may be thicker or thinner. In one embodiment, the body 102 includes a reflection reducing coating. In another embodiment, the body 102 is formed from a reflection reducing or non-reflective material. In FIG. 1, a containment shield 100 having a generally rectangular outline is shown whereas, in FIG. 4, a containment shield 100 having a generally ovular outline is shown. Other outline shapes are contemplated within the scope of the claims.

The body 102 has a plurality of folds 104A, 104B. Quadrant folds 104A divide the body 102 into quadrants. Bisecting folds 104B divide each quadrant generally in half. That is, the bisecting folds 104B extend at about a 45° angle in each quadrant from an origin of the quadrants formed by the quadrant folds 104A as shown in FIG. 1 or meet an edge of the body 102 halfway between two quadrant folds 104A (see, for example, FIG. 4). The quadrant folds 104A and the bisecting folds 104B are in opposite directions. That is, if the quadrant folds 104A operate to bring two points on the distal face 106 together, then the bisecting folds 104B operate to bring two points on the proximal face 108 together. Conversely, if the quadrant folds 104A operate to bring two points on the proximal face 108 together, then the bisecting folds 104B operate to bring two points on the distal face 106 together. The body 102 also includes a mounting hole 110 operable to engage the output housing of the surgical cutting instrument. A shaft of the surgical cutting instrument passes through the mounting hole 110 together with a portion of the output housing of the surgical cutting instrument, and a portion of the body 102 adjacent the mounting hole 110 frictionally engages the output housing of the surgical cutting instrument.

The body 102 may also include a plurality of slits 112 therethrough extending from an edge of the mounting hole 110. In one embodiment, each slits of the plurality of slits 112 extends along one of the plurality of folds 104A, 104B. In one embodiment, each slit 112 extends radially from a center point of the mounting hole 110. In another embodiment, each slit 112 extends perpendicularly from an edge of the mounting hole 110. In one embodiment, the mounting hole 110 has a diameter of approximately one half of an inch, and each slit 112 of the plurality of slits has a length of approximately one half of an inch. In one embodiment, the body 102 has a width of between approximately 8 and 10 inches. It is contemplated that these dimensions may vary to accommodate different sizes and types of surgical cutting instruments. In an alternative embodiment, there are no slits 112 extending from the mounting hole 110 (see, for example, FIG. 8).

Figure 2:
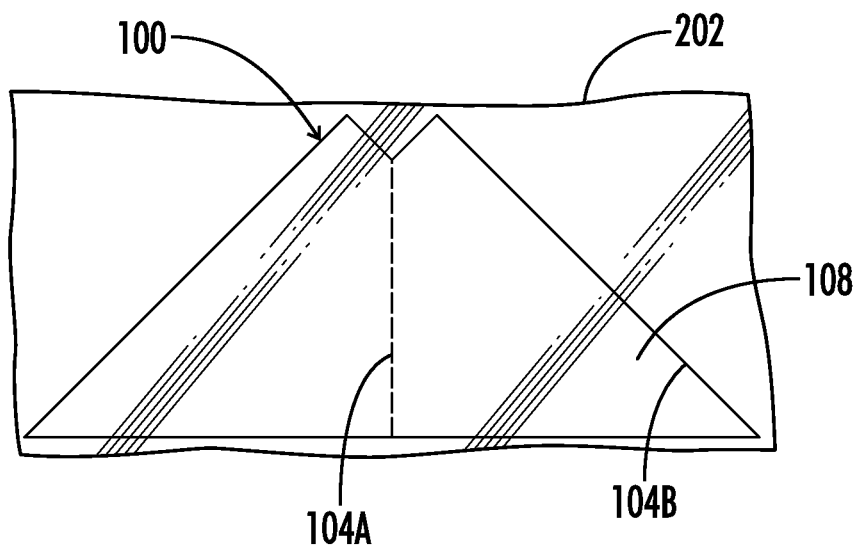
FIG. 2 is a side perspective view of a containment shield folded flat in sterile packaging

Referring to FIG. 2, the containment shield 100 is shown folded flat in a sterile package 202. To fold the containment shield 100 flat, the four quadrant folds 104A are brought together, and one pair of opposing quadrant folds are substantially flattened. The four bisecting folds 104B are folded such that portions of the distal face 106 adjacent each bisecting fold 104B are touching or in close proximity. The package 202 maintains the containment shield 100 in a substantially flat configuration within the sealed sterile enclosure of the package 202.

Figure 3:
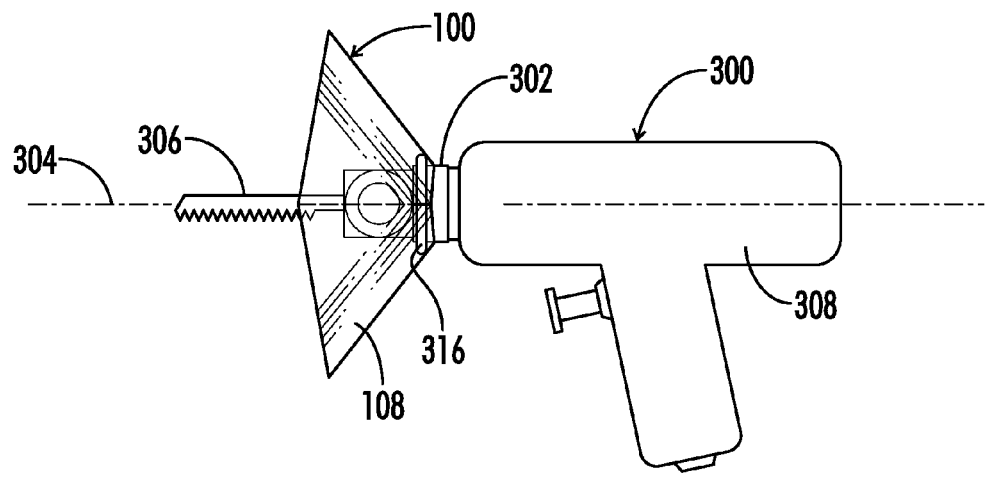
FIG. 3 is a side perspective view of a containment shield mounted on a surgical cutting instrument, particularly a saw.

Referring to FIG. 3, the containment shield 100 is mounted on an output housing 302 of a surgical cutting instrument 300. The distal face 106 is at an acute angle with respect to a longitudinal axis 304 through the mounting hole 110, and the distal face 106 faces toward a cutting device 306 of the surgical cutting instrument 300. The proximal face 108 is at an obtuse angle with respect to the longitudinal axis 304 and faces toward a housing side 308 of the surgical cutting instrument 300 opposite the cutting device 306 of the surgical cutting instrument 300. In one embodiment, the containment shield 100 further includes a collar 316 retaining the mounting hole 110 of the body 102 on the output housing 302 of the surgical cutting instrument 300. As shown, the collar 316 slips onto the output housing 302 after the containment shield 100 to prevent the containment shield 100 from slipping down the output housing 302 toward the cutting device 306. In another embodiment, the collar 316 slides onto the output housing 302 before the containment shield 100, and after the containment shield 100 is installed on the output housing 302, the collar 316 is slid over a portion of the body 102 adjacent the mounting hole 110 to increase the frictional engagement of the body 102 to the output housing 302. In one embodiment, the collar 316 is silicone rubber. The collar 316 may be turned inside out to roll down the output housing 302 onto the portion of the body 102 adjacent the mounting hole 302 (i.e., the portion free to lay flat against the output housing 302 due to slits 112).

Figure 5:
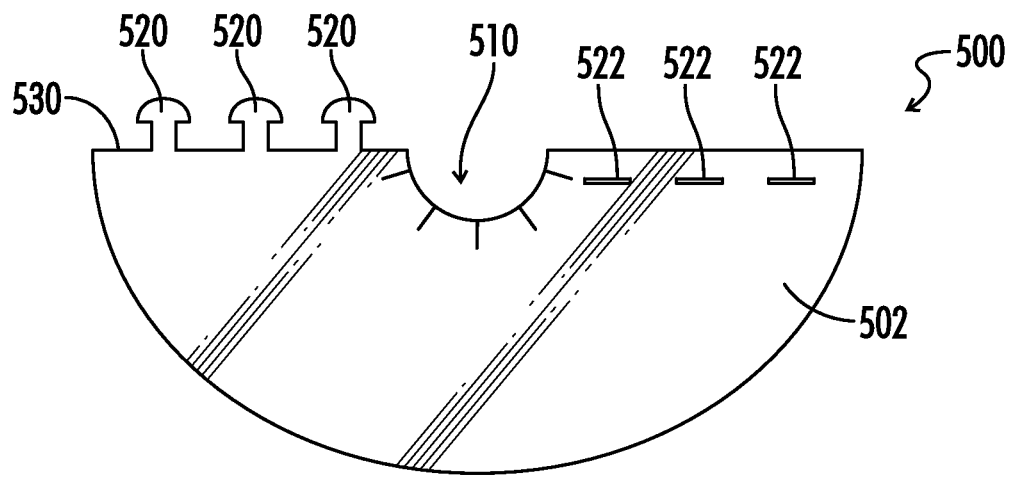
FIG. 5 is a perspective view of a distal face of a containment shield including tabs and slots in a flat configuration for packaging.
Figure 6:
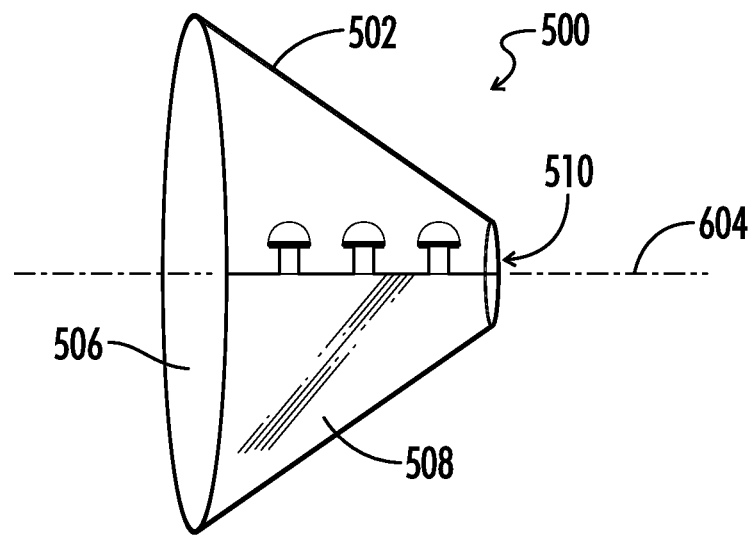
FIG. 6 is a perspective isometric view of a containment shield including tabs and slots in a three dimensional configuration for mounting on a surgical cutting instrument.

Referring to FIGS. 5 and 6, a containment shield 500 operable to mount on the output housing 302 of the surgical cutting instrument 300 includes a body 502 having a distal face 506, a proximal face 508, a tab 520, and a slot 522. As shown, the containment shield 500 has a plurality of tabs 520 and a plurality of corresponding slots 522. The body 502 is substantially transparent and has a generally consistent thickness such that the body 502 is pliable and resilient. In one embodiment of the body 502 having a generally consistent thickness, the body 502 is formed from a sheet of non-reflective plastic having a thickness of 0.025 mm+/− 0.005 mm. When the tab 520 is inserted into the corresponding slot 522, the containment shield 500 takes a generally conical form as shown in FIG. 6. When the tab 520 is not in the corresponding slot 522, the containment shield takes a generally flat form as shown in FIG. 5. The body 502 has a mounting hole 510 formed when the tab 520 is in the corresponding slot 522. The mounting hole 510 is operable to engage the output housing 302 of the surgical cutting instrument 300. When the tab 520 is in the corresponding slot 522, and the body 502 is mounted on the output housing 302 of the surgical cutting instrument 300, the distal face 506 is at an acute angle with respect to a longitudinal axis 604 through the mounting hole 510. The distal face 506 faces toward the cutting device 306 of the surgical cutting instrument 300. The proximal face 508 is at an obtuse angle with respect to the longitudinal axis 604 and faces toward a housing 308 of the surgical cutting instrument 300 opposite the cutting device 306 of the surgical cutting instrument 300.

In the embodiment illustrated in FIG. 5, the body 502 has an outline that is substantially semicircular (e.g., a half-moon shape). The tab 520 extends from the generally straight edge 530 of the outline of the body 502. The slot 522 corresponding to the tab 520 is adjacent the straight edge of the outline of the body. That is, the slot is through the body 502 and set back from the straight edge 530. Disregarding the tab 520 and slot 522, the outline of the body 502 is substantially symmetrical about an axis. The axis thus divides the outline of the body 502 into a first half and an opposing, symmetrical second half. The straight edge 530 of the outline in the first half appears as a mirror image about the axis in the second half. For example, if the straight edge 530 is perpendicular to the axis in the first half, then it is also perpendicular to the axis in the opposing second half. However, if the straight edge is at 45 degrees with respect to the axis in the first half, then the straight edge is at 45 degrees with respect to the axis in the second half. The tab 520 extends from the straight edge in the first half of the outline of the body. The slot 522 is adjacent the straight edge 530 in the second half of the outline of the body 502. In an alternative embodiment, the outline of the body 502 is fan shaped such that when the tabs 520 are in the corresponding slots 522, a cross section of the containment shield 100 is substantially square or rectangular.

In one embodiment, a method of using a containment shield begins with removing the containment shield from packaging. The shield includes a body that is substantially transparent and as a generally consistent thickness such that the body is pliable and resilient. The body is substantially planar and sterile when in the package. The method then continues with forming the containment shield into a three-dimensional shape having a distal face and a proximal face. The third step of the method is engaging a mounting hole of the containment shield on to the output housing of the surgical cutting instrument such that the distal face is at an acute angle with respect to a longitudinal axis through the mounting hole and faces toward a cutting device of the surgical cutting instrument. The proximal face is at an obtuse angle with respect to the longitudinal axis and faces toward a housing side of the surgical cutting instrument. In one embodiment, forming the containment shield into the three-dimensional shape includes flexing a plurality of folds of the body of containment shield. In an alternative embodiment, forming the containment shield into the three-dimensional shape includes engaging a tab of the body with a corresponding slot in the body to form the containment shield into a generally conical shape. The method may also include operating the surgical cutting instrument to cut biological material, and replacing the containment shield with another containment shield (i.e., repeating the removing, forming, and engaging steps of the method) when visibility through the containment shield is reduced due to debris from cutting the biological material.

Figure 7:
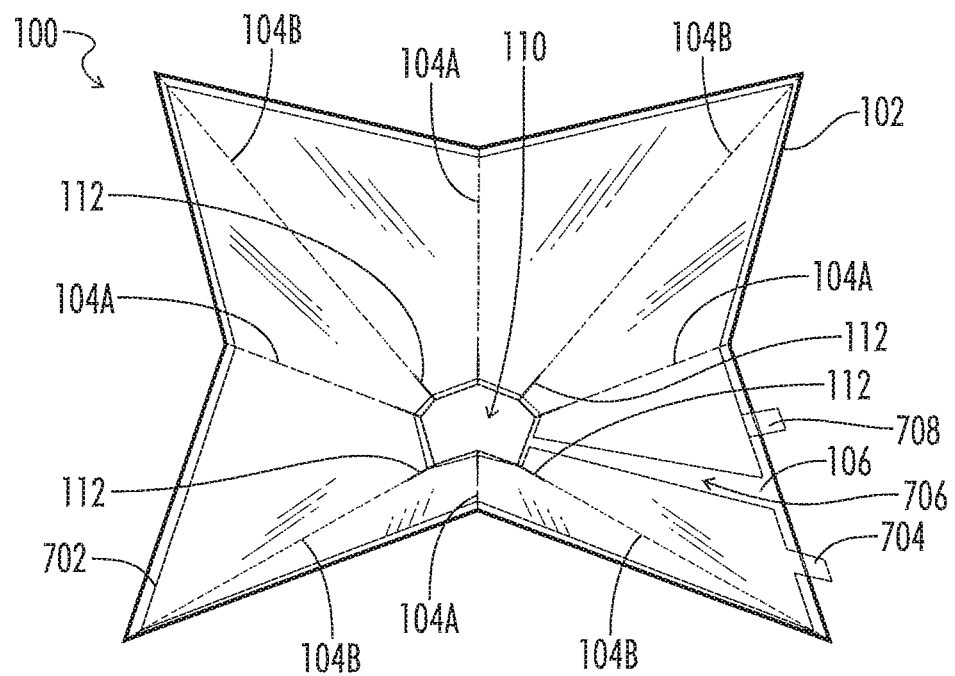
FIG. 7 is a perspective side view of a containment shield having removable layers.

Referring to FIG. 7, a containment shield 100 has one or more layers of film on a distal face 106 of the body 102. In one embodiment, a distal layer of film 702 is a thin layer of plastic adhered to the body 102 or underlying layer of film by static cling or a light duty adhesive. In one embodiment, the film is 0.5 mil thick polyvinyl chloride (PVC). When visibility through the distal layer 702 of the plurality of layers becomes obscured by spatter, operating room personnel can peel the layer of film 702 from the containment shield 100, resulting in a substantially spatter free containment shield. The film has a peel tab 704 protruding from the edge of the body 102. Successive tabs 708 corresponding to successively less distal layers of film are adjacent the peel tab 704 corresponding to the most distal layer 702. In one embodiment, the most distal layer of film 702 has a slit 706 therethrough from an outer edge of the layer of film to an inner edge adjacent the mounting hole 110. The slit 706 allows the layer of film 702 to be peeled from the containment shield 100 with reduced interaction with the cutting device 306 of the cutting instrument 300 which helps to prevent injury to operating room personnel. Although the distal layer of film 702 is shown as inset from the edges of the body 102, it is contemplated that the edges of the layers of film may be inset or coextensive with the edges of the body 102.

Figure 8:
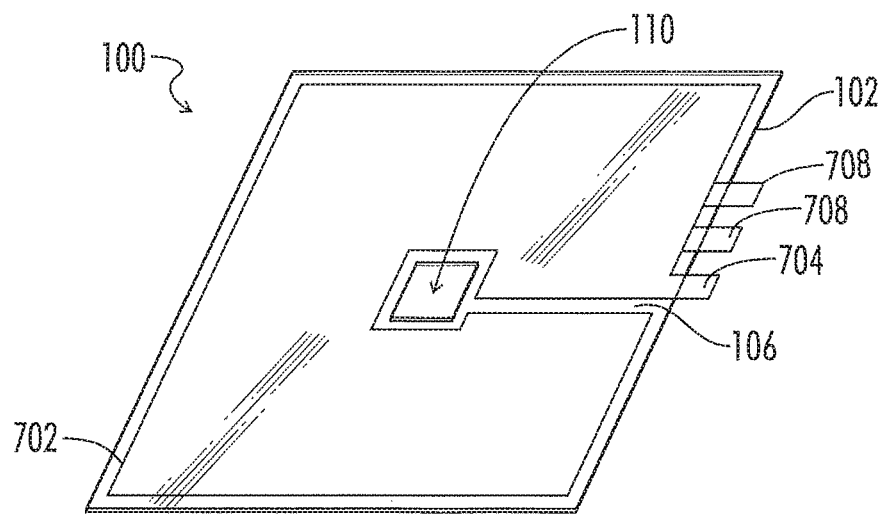
FIG. 8 is a perspective side view of a flat containment shield having removable layers.

Referring to FIG. 8, a containment shield 100 has a plurality of layers of film on a distal face 106 of the body 102. The distal layer of film 702 is a thin layer of plastic adhered to the body 102 or underlying layer of film by static cling. The distal layer of film 702 has a peel tab 704 protruding from the edge of the body 102. Successive tabs 708 corresponding to successively less distal layers of film are adjacent the peel tab 704 corresponding to the most distal layer 702. In one embodiment, the most distal layer of film 702 has a slit 706 therethrough from an outer edge of the layer of film to an inner edge adjacent the mounting hole 110. Additionally, the mounting hole 110 in this embodiment may be substantially square and does not have slits extending radially therefrom. This style of mounting hole 110 may be used to mount on a square output housing, or for mating with a collar that retains the containment shield 100 on a surgical cutting instrument. Although the outline of the containment shield 100 of FIG. 8 is substantially square, it is contemplated that the containment shield 100 may have a generally circular, rectangular, or oblong outline. In one embodiment, a side of the square mounting hole 110 of the containment shield 100 of FIG. 8 is 3/16". In an alternative embodiment, the mounting hole 110 is circular with a diameter of 3/16".

Figure 9:
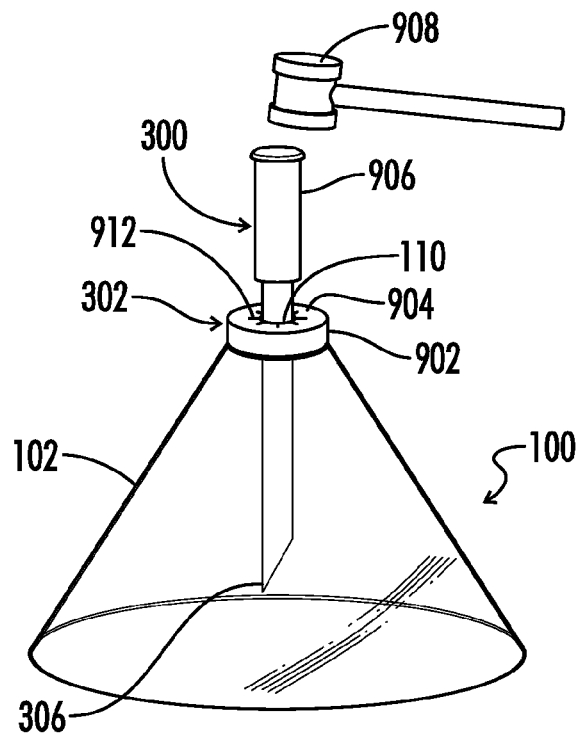
FIG. 9 is perspective side view of a containment shield mounted on a surgical cutting instrument, particularly a chisel.

Referring to FIG. 9, the containment shield 100 includes the body 102 and a collar 302. In one embodiment, the collar 302 has a collar top 904 and a neck 902 extending therefrom toward the body 102. The neck 902 joins the collar top 904 to the body 102. In one embodiment, the neck 902 is integral with the collar top 904. The neck 902 may be of the same material as the collar top 904, or the neck 902 may be a harder material that helps the containment shield 100 and collar top 904 maintain their shape. Alternatively, the neck 902 may be welded or affixed to the collar top 904 with an adhesive. Similarly, the next 902 is affixed to the body 102 via a welding process (e.g., ultrasonic welding) or via an adhesive. In the embodiment shown in FIG. 9, the collar top 904 of the collar 302 includes a mounting hole 110 having a diameter of approximately 3/16 of an inch with slits 912 extending radially outward. In FIG. 9, the surgical cutting instrument 300 shown is a chisel 906 (e.g., a bone chisel) and a hammer 908.

Figure 10:
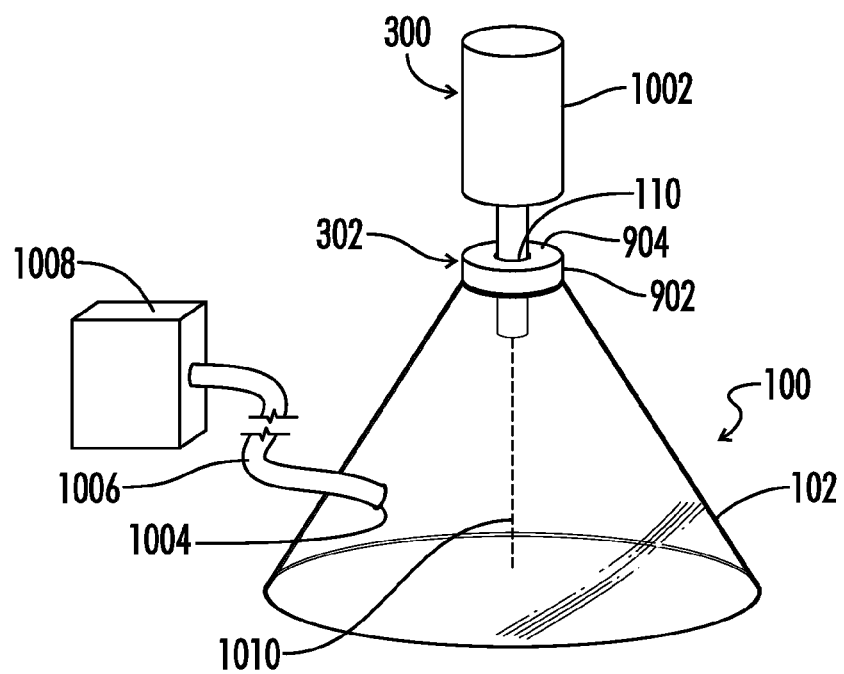
FIG. 10 is a perspective side view of a containment shield with a suction port mounted on a surgical cutting instrument, particularly a laser.

Referring to FIG. 10, a laser 1002 is shown as the surgical cutting instrument 300. The laser 1002 can generate both spatter and smoke when high energy pulses of light 1010 are emitted from the laser 1002 and impinge on biological material. In certain surgeries, the smoke can spread pathogens (e.g., pathogens that cause warts) to operating room personnel. Therefore, in one embodiment, the collar 302 fits tightly (i.e., elastically) around the output housing of the laser 1002 to substantially seal to the output housing of the laser 1002. In optional embodiments, the collar top 904 does not include slits in the embodiment shown in FIG. 10 in order to improve sealing of the containment shield 100 about the output housing of the laser 1002. The body 102 includes a suction port 1004 for receiving a suction tube 1006 from a suction device 1008. The suction tube 1006 may pass through the suction port 1004 or a fitting may couple the suction tube 1006 to the suction port 1004. The suction device 1008 may thus evacuate harmful smoke from the area adjacent the distal face of the containment shield 100 and filter pathogens and toxins from the air, reducing or eliminating the health risk to operating room personnel during certain surgeries or procedures.

In optional embodiments, the containment shield 100 is made of a material that filters certain wavelengths of light (e.g., the wavelength of the light pulses emitted by the laser 1002). When used with the laser 1002, this may eliminate the need for operating room personnel to wear protective lenses for filtering the wavelength of the laser or at least provide an additional layer of protection for the eyes of operating room personnel from the emitted high energy pulses of light 1010. Providing a seal between the containment shield 100 and the surgical cutting device 300 and the suction port 1004 may also be particularly advantageous for laser coagulators and cauterizing instruments. In other optional embodiments, the device may have a coating that can block or reduce laser light transmission through the device to protect or minimize light exposure to operating room personnel.

It is contemplated that an output housing of a surgical cutting instrument may be generally integral with the housing of the surgical cutting instrument. It is also contemplated within the scope of the claims that the mounting hole may be any size or shape (e.g., square, circular, or otherwise) so as to generally correspond to a class or type of surgical cutting instruments. Further, the overall size of the containment shield may vary according to the intended surgical cutting instrument. Additionally, it is contemplated that "conical" or "generally conical" includes a shape generally corresponding to a pyramid within the scope of the claims.

Furthermore, while the device is described as being used for surgical applications, particularly orthopedics, the device can also be used for a variety of other applications as well. This included various different medical procedures, dental surgery, veterinary medicine, organ transplants and harvesting, and also forensic applications.

Additionally, while in a variety of optional embodiments of the invention, the device may be formed from a flat sheet, in optional further embodiments, the device may maintain a three-dimensional shape. In such optional embodiments, the three dimensional shape may be conical or trapezoidal or have some other non-flat design. Such optional embodiments can possess many of the other traits, from rigidity to transparency of the other optional embodiments.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although there have been described particular embodiments of the present invention of a new and useful CONTAINMENT SHIELD FOR SURGICAL INSTRUMENTS, it is not intended that such references be construed as limitations upon the scope of this invention except as set forth in the following claims.

What is claimed is:

1. A containment shield operable to mount on an output housing of a surgical cutting instrument, said containment shield comprising:
   a body having a distal face, a proximal face, a tab, and a slot wherein:
      the body is transparent and has a generally consistent thickness such that the body is pliable and resilient;
      the body is generally conical when the tab is in the slot;
      the body is flat when the tab is not in the slot;
      the body has a mounting hole formed when the tab is inserted in the slot operable to engage the output housing of the surgical cutting instrument;
      the body having a suction port operable to engage a suction tube of a suction device;
      the body does not pass light having a wavelength of approximately 10.6 µm or 1.6 µm;
   and
      when the tab is in the slot and the body is mounted on the output housing of the surgical cutting instrument, the distal face is at an acute angle with respect to a longitudinal axis through the mounting hole and facing toward a cutting device of the surgical cutting instrument while the proximal face is at an obtuse angle with respect to the longitudinal axis and facing toward the output housing side of the surgical cutting instrument.

2. The containment shield of claim 1, further comprising a package, wherein the containment shield is flat and sterile within a package.

3. The containment shield of claim 1, wherein the body further comprises a plurality of slits therethrough, each slit of said plurality of slits extending radially from a center point of the mounting hole.

4. The containment shield of claim 1, wherein the body further comprises a plurality of slits therethrough, each slit of said plurality of slits extending perpendicularly from an edge of the mounting hole.

5. The containment shield of claim 1, wherein the body further comprises a reflection reducing coating.

6. The containment shield of claim 1, wherein the mounting hole is operable to receive a shaft of the surgical cutting instrument.

7. The containment shield of claim 1, wherein:
   the mounting hole has a diameter of approximately one half of an inch; and
   the body further comprises a plurality of slits therethrough, each slit of the plurality of slits extending from an edge of the mounting hole, wherein each slit has a length of approximately one half of an inch.

8. The containment shield of claim 1, wherein when the tab is not in the slot and the body is laid flat:
   the body has an outline that is semicircular;
   the tab extends from a generally straight edge of the outline of the body; and
   the slot is adjacent the straight edge of the outline of the body in a half of the outline of the body opposite a half of the outline of the body of the tab.

9. The containment shield of claim 1, wherein the shield further comprises a removable layer of film on the distal face of the body.

10. The containment shield of claim 9, wherein the removable layer of film further comprises a peel tab protruding from an edge of the body.

* * * * *